United States Patent
Ito et al.

(10) Patent No.: US 6,369,382 B1
(45) Date of Patent: *Apr. 9, 2002

(54) MASS SPECTROMETRY AND MASS SPECTROSCOPE

(75) Inventors: Shinya Ito, Hitachinaka; Noriko Minakawa, Naka-gun, both of (JP)

(73) Assignee: Hitachi, Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/075,829

(22) Filed: May 12, 1998

(30) Foreign Application Priority Data

May 16, 1997 (JP) ............................................. 9-126715

(51) Int. Cl.$^7$ ............................ B01D 59/44; H01J 49/00
(52) U.S. Cl. ...................... 250/281; 250/282; 73/53.01
(58) Field of Search ................................. 250/281, 282, 250/283, 288, 252.1 R; 202/117; 73/53.01

(56) References Cited

U.S. PATENT DOCUMENTS

| 4,008,388 A | * | 2/1977 | McLafferty et al. ........ 250/281 |
|---|---|---|---|
| 4,507,555 A | * | 3/1985 | Chang ........................ 250/282 |
| 4,808,818 A | * | 2/1989 | Jung ........................... 250/282 |
| 5,072,115 A | * | 12/1991 | Zhou .......................... 250/282 |
| 5,352,891 A | * | 10/1994 | Monnig et al. .............. 250/282 |
| 5,523,565 A | * | 6/1996 | Federer et al. .............. 250/288 |
| 5,600,134 A | * | 2/1997 | Ashe et al. .................. 250/288 |
| 5,742,525 A | * | 4/1998 | Ye ......................... 250/252.1 R |
| 5,744,702 A | * | 4/1998 | Roussis et al. ............ 73/53.01 |
| 5,862,512 A | * | 1/1999 | Voorhees ....................... 702/2 |

* cited by examiner

Primary Examiner—Bruce Anderson
(74) Attorney, Agent, or Firm—Kenyon & Kenyon (57) ABSTRACT

The mass spectrum of a reference sample is stored at the time of preparing a calibration curve, and the mass spectrum of the reference sample that is stored is compared with the mass spectrum of an unknown sample at the time of measuring the unknown sample, in order to judge the reliability of the results of determination. Since the reliability of the results of determination is evaluated based on the numerical values, the evaluation does not change depending upon the judgment by the person who conducts the analysis, and certain evaluation is obtained.

11 Claims, 12 Drawing Sheets

MASS SPECTROMETRY AND MASS SPECTROSCOPE

BACKGROUND OF THE INVENTION

1. Field of the Invention

The present invention relates to mass spectrometry and a mass spectroscope.

2. Description of the Prior Arts

In recent years, a mass spectroscope has been often used for analysis of a sample. A mass spectroscope is used in a manner that a sample is ionized, and the mass is selected by scanning an electric field or a magnetic field thereby to detect ions that are selected by scanning. An output (mass spectrum) is thus obtained for the mass. The sample is ionized by imparting electric charge to the sample, such as by causing electrons to impinge onto the sample (EI method), spraying the sample under a high voltage (electrospray method/ESI method) or chemically ionizing the sample (atmospheric-pressure chemical ionization method/APCI method). Such technologies have been disclosed in, for example, Japanese Patent Laid-Open No. 9359/1989.

As described above, when electric charge is imparted to electrons, electron impingement, high voltage or large chemical energy are involved. Therefore, impurities are inevitably produced. By the EI method, for example, the sample is destroyed by the bombardment with electrons and, hence, ions having masses different from that of the sample to be measured are produced in large amounts. Such impurities are mixed into the sample to be measured and cause the measurement precision to lower. In particular, when impurities adhere to the interior of the mass spectroscope and are accumulated to contaminate the interior of the mass spectroscope, the measurement precision is greatly deteriorated and the results of analysis become no longer reliable.

SUMMARY OF THE INVENTION

The object of the present invention is to provide a mass spectrometry and a mass spectroscope capable of verifying the reliability of the results of analysis.

In order to accomplish the above-mentioned object according to the present invention, the sample is ionized, the ionized sample is separated depending upon the mass, the quantity corresponding to a specific mass number included in the sample as a result of separation is measured, common detection items of the separated sample and a different sample are compared, or different detected quantities in the same sample are compared, and the data on reliability are output based upon the comparison.

Preferably, the mass spectrum of a reference sample is stored at the time of measuring the reference sample, and the mass spectrum of the reference sample that is stored is compared with the mass spectrum of an unknown sample at the time of measuring the unknown sample, in order to judge the reliability of whether the quantitative object component is correctly measured or not.

In a general mass spectroscope, furthermore, it is preferable that the mass spectra having close densities are compared with each other though the pattern of mass spectrum varies depending upon the concentration of a sample due to chemical ionization reaction among sample molecules. This makes it possible to minimize the influence due to a change in the pattern of the mass spectrum caused by a change in the concentration and, hence, to improve the reliability of the results of determination. In particular, it is necessary to calculate the concentration of an unknown sample from a calibration curve, and to compare a reference sample having a concentration closest to the concentration of the known sample with the unknown sample. Whether the object component is quantitatively determined correctly or not is judged by comparing numerical values of the degrees of similarity of the mass spectrum of the reference sample to the mass spectrum of the unknown sample, the difference in the evaluation of reliability of the results of quantitative determination that varies depending upon the degree of skill of the person who conducts the analysis. When the concentration of the sample lowers, the reliability of the degree of analogy is degraded by the influence of peaks such as the background peak, and the adjacent peaks, and by random noise. However, the reliability of the degree of analogy is improved by purification by automatically removing the background peak, in which no peak is detected while the component is being held and the peaks attributed to components held for different times, from the mass spectra of the reference sample and the unknown sample.

Preferably, furthermore, the degree of similarlity of the peak of the object component is verified by comparing the half-width of the peak/the peak intensity of the object component in the mass chromatogram of mass number for determination of the reference sample and the unknown sample. This makes it possible to examine the influence caused by the contamination of the apparatus and the deterioration of the column and, hence, to judge the reliability of the results of determination.

Preferably, furthermore, the intensity ratio of the mass numbers is found at which a characteristic peak is obtained in the object component, and is compared with the intensity ratio of an unknown sample. This makes it possible to verify whether the mass number for determination is separated in terms of mass from the adjacent peaks and, hence, to know the influence from the peaks of other components.

Preferably, as a report of reliability, the degree of analogy calculated between the mass spectrum of the reference sample that is automatically purified and the mass spectrum of the unknown sample. This enables the person who conducts the analysis to confirm the reliability of the results of determination in terms of numerical values. By displaying the normalized spectra of the two mass spectra and the differential spectrum between the two mass spectra, furthermore, the person who conducts the analysis can visually confirm the reliability; i.e., the person who conducts the analysis can verify the validity of the results of determination based upon the judgment by both the numerical values and the screen.

On the screen for reporting reliability, preferably, the mass used for the determination and the mass used for a reference are distinctly displayed in different colors or using different symbols or different kinds of line on the mass spectrum of the unknown sample and on the mass spectrum of the reference sample that are automatically purified or on the differential spectrum thereof. Then, the person who conducts the analysis can visually confirm whether the object component is quantitatively separated from the adjacent peaks on the chromatogram, precluding unadequate quantitative mass.

Preferably, the mass spectrum of the reference sample at the time of generating the calibration curve is compared with the mass spectrum for confirming the reliability that has been registered in advance, and the intensity ratio of the mass spectra at the same concentration and the degree of analogy are used as indexes of reliability of the apparatus.

This makes it possible to verify the influence of the interface unit, the influence of a drop in the sensitivity due to contamination of the ion source and deterioration in the detector and the influence of a change in the mass spectrum pattern. Therefore, the person who conducts the analysis can easily know the timing of maintenance of the apparatus. If the value is greater than a predetermined value, it is ensured that the apparatus is in a state in which quantitative analysis can be done.

BRIEF DESCRIPTION OF THE DRAWINGS

FIGS. 4(a)–(c) is a diagram showing mass spectra;

FIGS. 6(a)–(d) is a diagram illustrating the operation of automatic purification;

FIGS. 11(a)–(c) is an explanatory diagram illustrating the influence of disturbing components.

PREFERRED EMBODIMENT

An embodiment of the present invention will be described with reference to the drawings.

Figure 2:
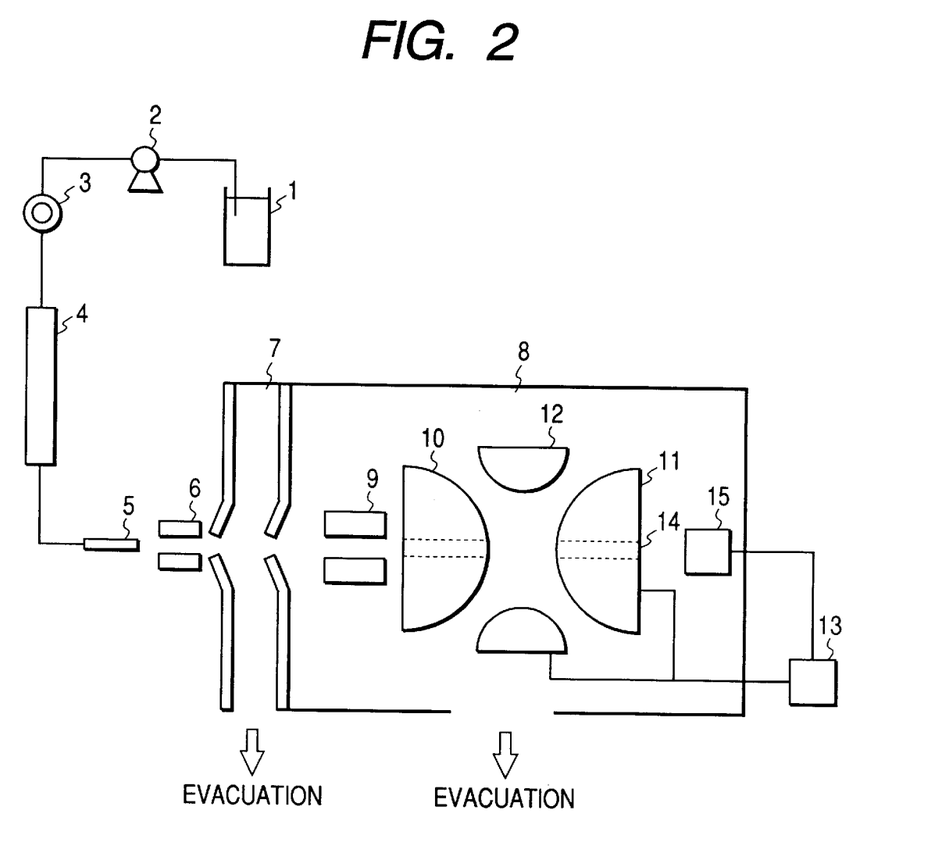
FIG. 2 is a diagram illustrating the constitution of the whole apparatus.
Figure 3:
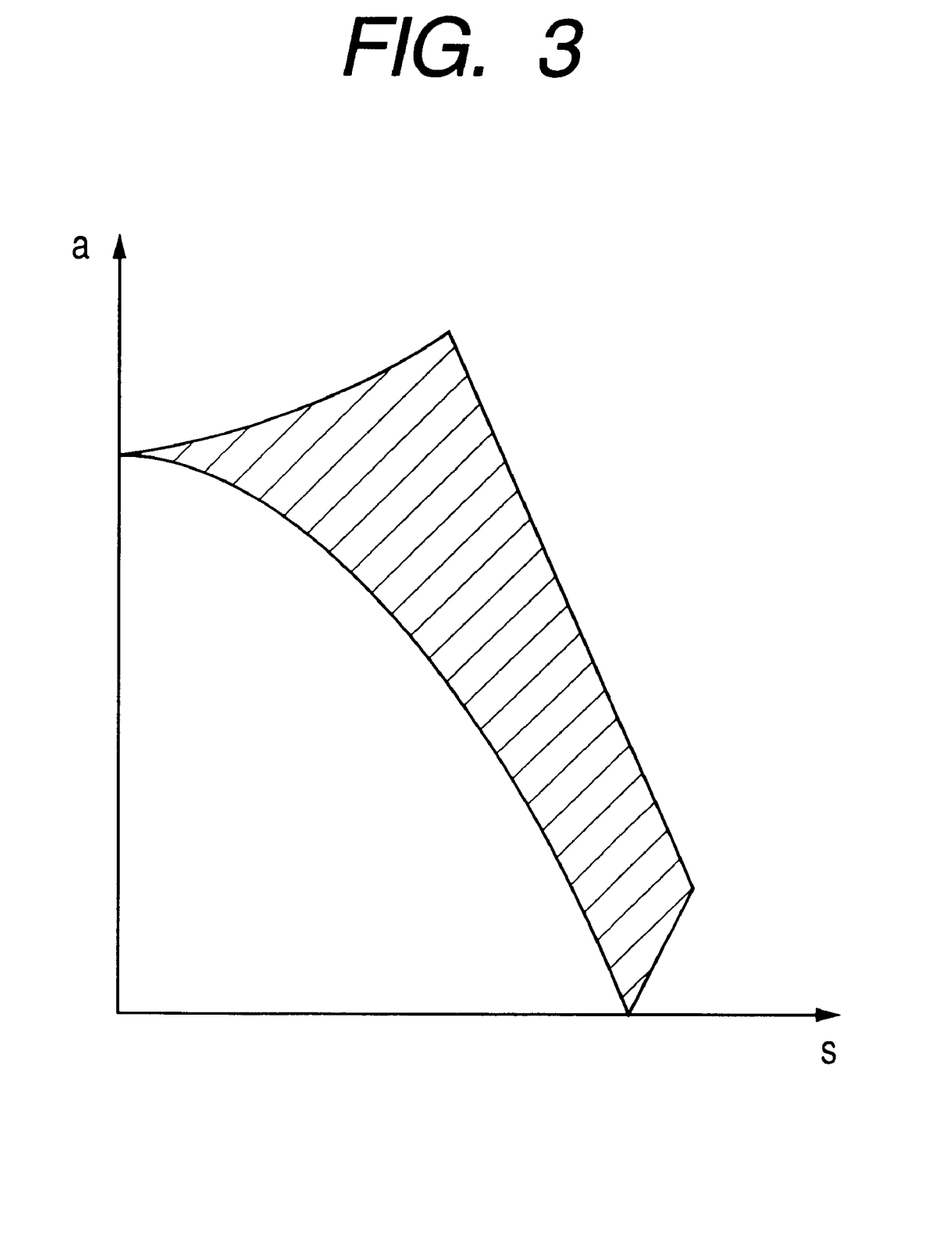
FIG. 3 is a diagram showing curves defining a stable trap space.

FIG. 2 schematically illustrates an LC-directly-coupled ion trap mass spectroscope. A mobile phase solvent stored in a solution bottle 1 is sent by a pump 2 into an analytical column 4 through a filling port 3. A sample is introduced by a micro-syringe or the like through the filling port 3. The introduced sample flows forward through the analytical column 4 and is separated into components. The sample component solution that has passed through the analytical column 4 is sent to an ESI probe 5 to which a high voltage is applied, and is sprayed from the tip of the probe into the open air as droplets having electric charge. The droplets repetitively collides with molecules in the open air; i.e., the diameters of the droplets decrease and, finally, ions are released into the open air. The produced ions are heated by a heater 6 and are introduced, through a slit, into an intermediate-pressure chamber 7 that is evacuated by a vacuum pump. Ions are further introduced into a vacuum chamber which is evacuated by a vacuum pump and in which a mass spectroscope is installed. Ions are then introduced into a space surrounded by end cap electrodes 10, 11 of a lens 9 and a doughnut-shaped ring electrode 12. These electrodes have a parabolic shape in cross section. Ions are stably trapped by a high frequency of about 1 MHz applied to the ring electrodes 12. A DC voltage U and a high-frequency voltage $V \cos \Omega t$ are applied across the electrodes thereby to establish a quadruple electric field in the space among the electrodes. The stability of trajectories of ions trapped in the electric field is determined by the size of the apparatus (inner diameter r0 of the ring electrode), the DC voltage U applied to the electrodes, the amplitude V and angular frequency $\Omega$ of a high-frequency voltage applied to the electrodes, and the values a, q given by the mass/charge ratio m/Z of ions (formula 1), $$a = 8eU/r0^2 \Omega^2 \times z/m$$

$$q = 4eV/r0^2 \Omega^2 \times z/m \quad (1)$$

where z is the ionic valance of the ion, m is the mass and e is the elementary charge. FIG. 3 is a diagram illustrating a region where the values a and q give stable trajectories in the space among the ion-trapping electrodes. All ions in the stable region vibrate stably in the space among the electrodes. The ions accumulated in the electrodes are released out of the trap through a hole 14 made at the center of the end cap electrodes upon changing the high-frequency voltage (amplitude) applied to the ring electrodes. The released ions are detected by a detector 15 to obtain a mass spectrum using a data processor 13. The voltages are applied to the end cap electrodes 10, 11 and to the ring electrodes from the data processor 13.

Figure 4:
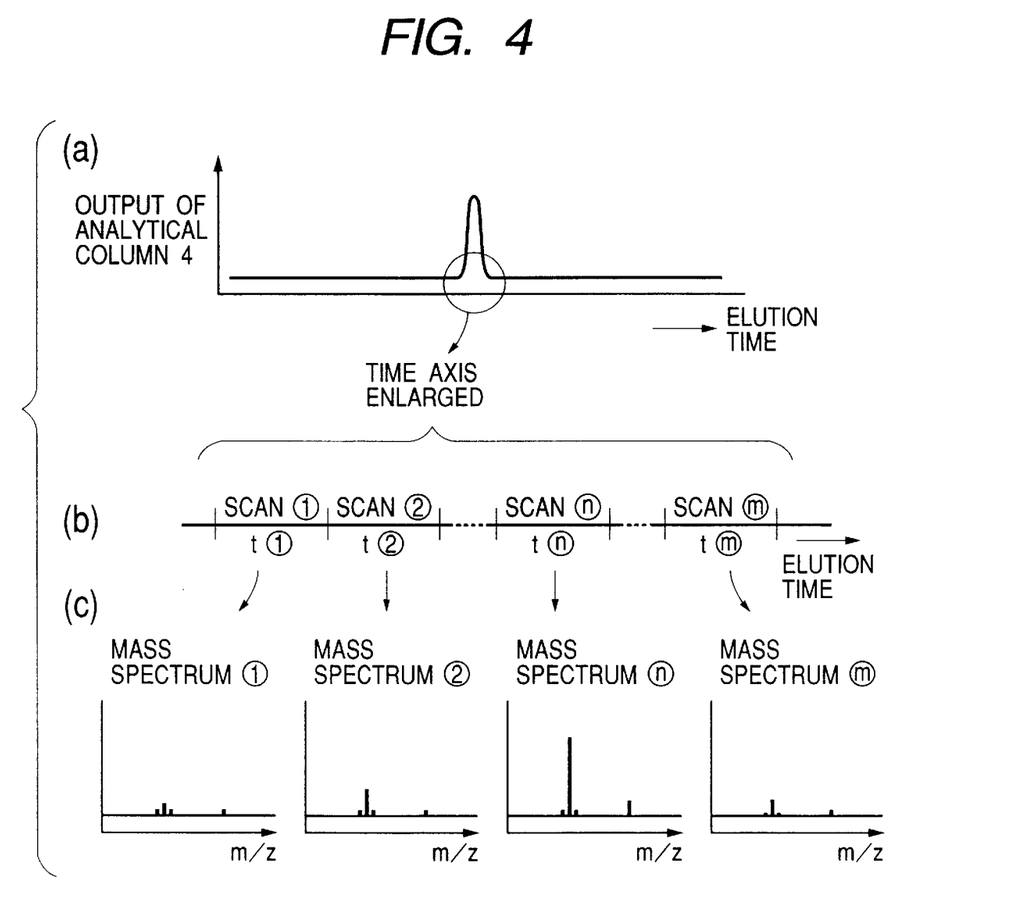

FIG. 4 illustrates the outputs of mass spectrum. As the sample passes through the analytical column 4, an output is produced for the elution time as shown in FIG. 4(a). Meanwhile, the sample separated by the analytical column 4 is further separated depending upon the mass when the voltages applied to the end cap electrodes 10, 11 and to the ring electrodes 12 are varied. In this separation, a predetermined mass is scanned repetitively at short time intervals. Referring to FIG. 4(b), for example, the scanning is effected for periods of time t(1), t(2), . . . , t(n), . . . , t(m). In response thereto, a mass spectrum is displayed on the data processor 13.

Figure 1:
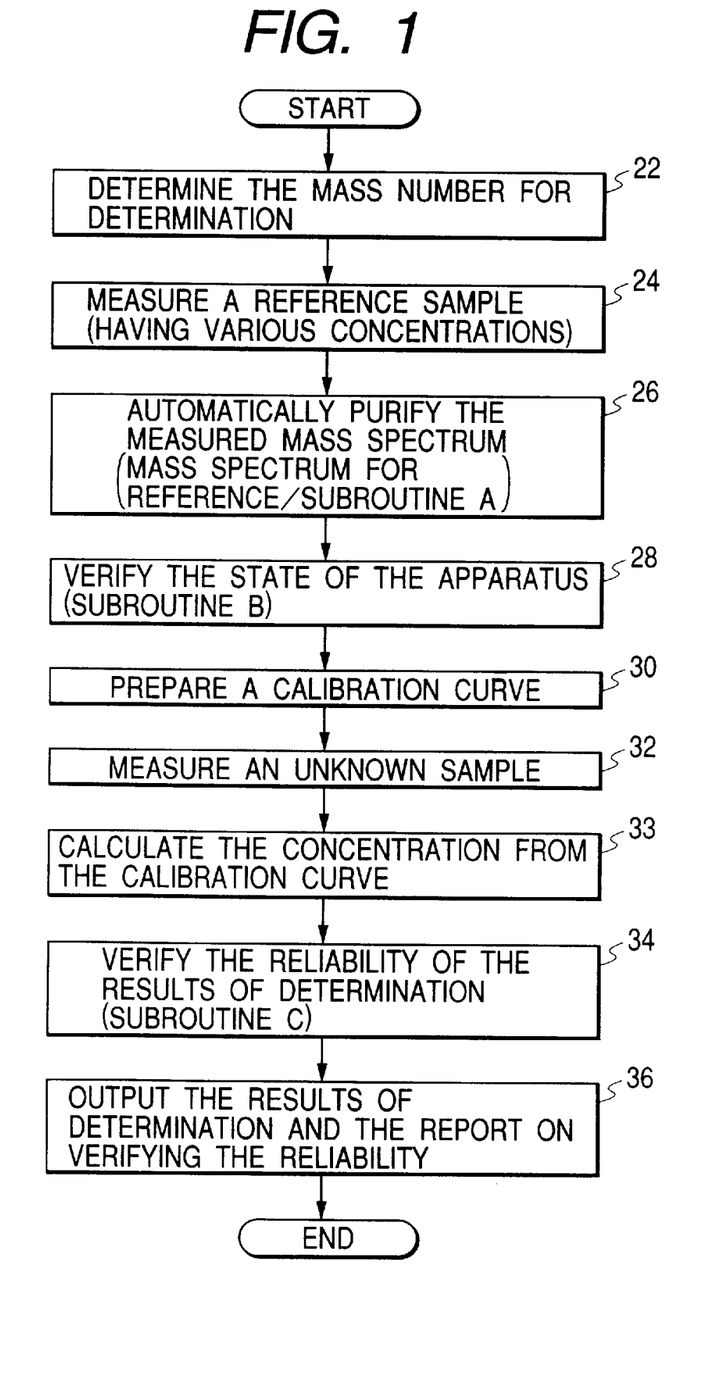
FIG. 1 is a flowchart illustrating the quantitative analysis.

With reference to FIG. 1, a procedure for determination using the mass spectroscope according to the present invention will be described below. First, the operator determines the object determination component and the mass number to be used for the determination, which are then input to, and stored in, the data processor 13 (step 22). Next, the reference samples of object component having different concentrations are measured (step 24). Their mass spectra are automatically purified and are stored for reference (step 26, subroutine A).

Figure 5:
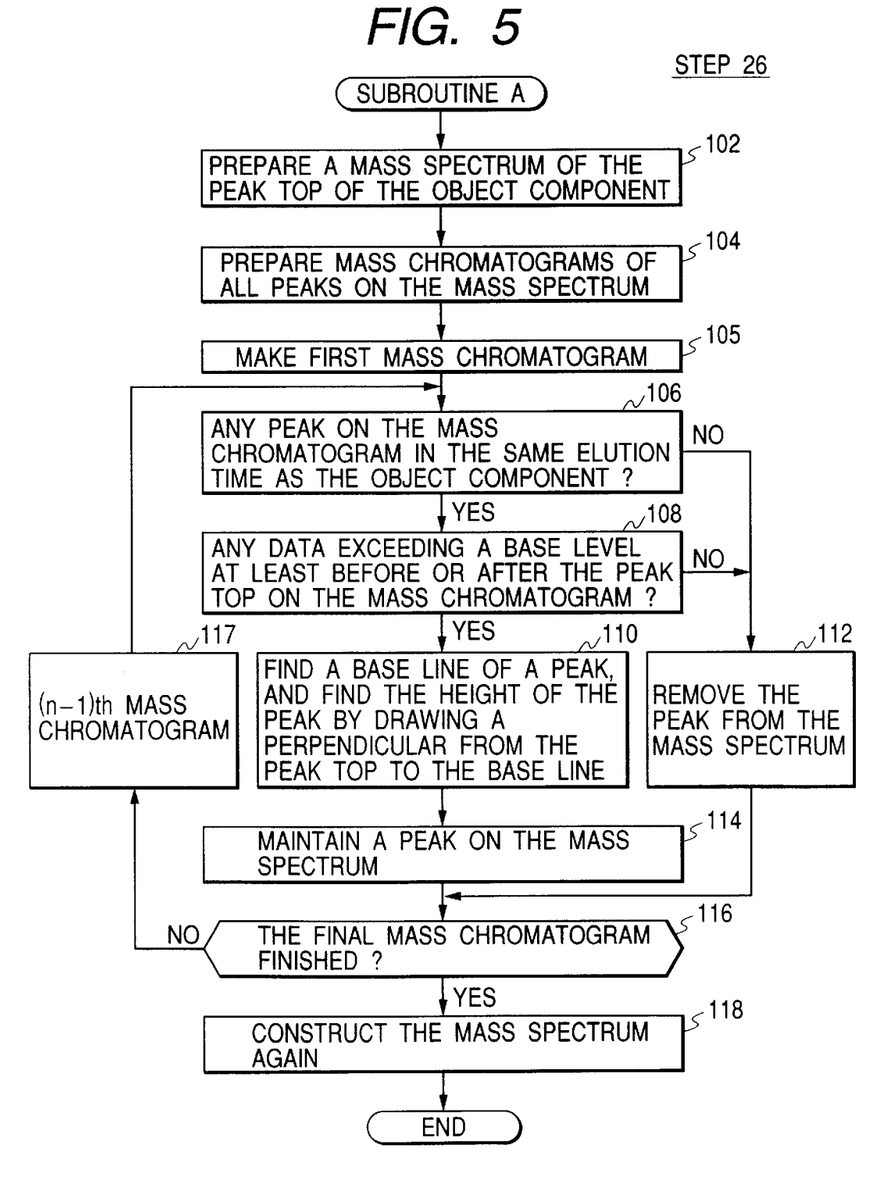
FIG. 5 is a flowchart illustrating the automatic purification in detail.
Figure 6:
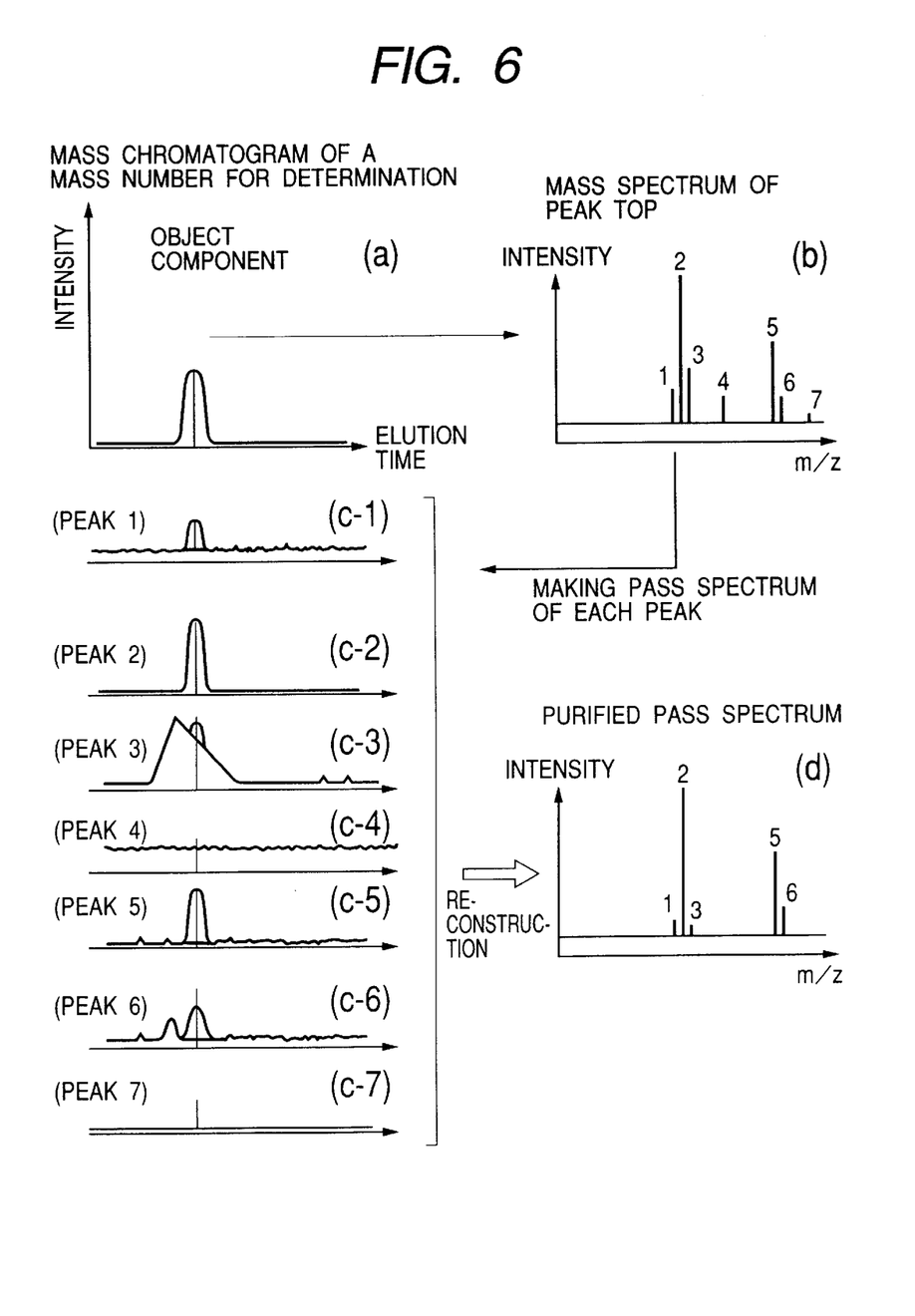

FIG. 5 is a flowchart of a subroutine for automatically purifying a mass spectrum. First, the peak of an object component is selected from a mass chromatogram (FIG. 6(a)) of the mass number for determination to make a mass spectrum of the peak top thereof (FIG. 6(b), step 102). Then, mass chromatograms of all peaks (peak 1 to peak 7) on the mass spectrum are generated (step 104). For the first mass chromatogram (FIG. 6(c-1), step 105), it is verified whether there is a peak in the same elution time as that of the peak of the object component on the mass chromatogram of the mass number for determination. When no peak exists in the same elution time as the peak on the mass chromatogram of the mass number for determination (step 106), i.e., when a peak seems to exist on the mass spectrum due to the background or when the elution time is different though there exists a peak, it is judged that the peak is not the one of the object component, and the peak is removed from the mass spectrum (step 112). When there exists a peak on the mass chromatogram in the same elution time, the procedure proceeds to the next verification.

Next, it is verified whether a data exceeding a base level exists at least before or after the peak top of a peak on the mass chromatogram existing in the same elution time as the object component, like, e.g., in FIG. 6(c-3) (step 108). That is, when the peak on the mass chromatogram is formed by only a single data, like in, for example, FIG. 6(c-7), it is judged that the peak is attributed to random noise which is different from the object component, and the peak is removed from the mass spectrum (step 112). When the peak is constituted by a plurality of data, it is judged that the peak is not attributed to random noise but results from the object component.

Figure 7:
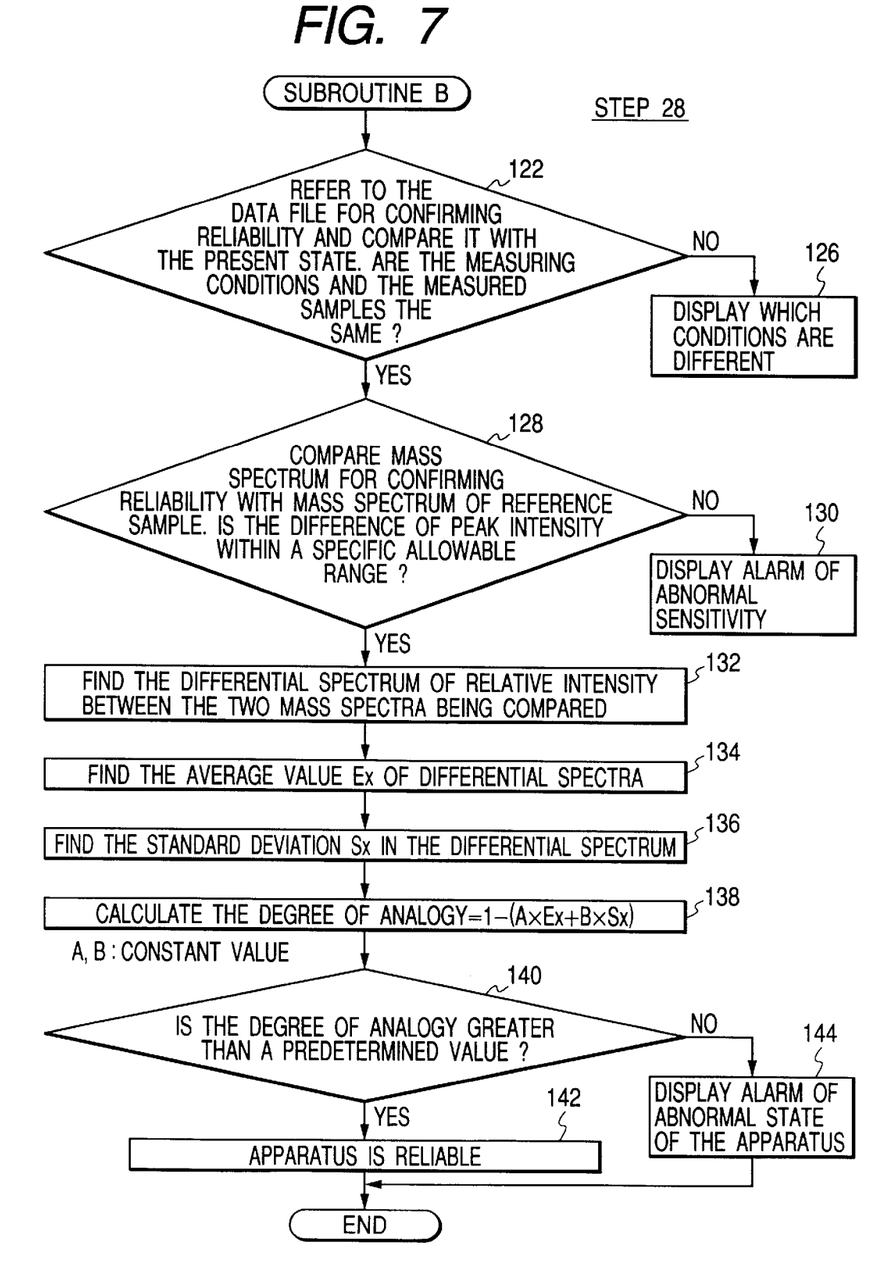
FIG. 7 is a flowchart illustrating the verification in detail.

Therefore, a base line of the obtained peak is found, and the height of the peak is found by drawing a perpendicular from the peak top to the base line (step 110). Then, a peak is maintained on the mass spectrum (step 114). The above-mentioned operation is repeated up to the final chromatogram (steps 116, 117), the mass spectrum is constructed again, and the spectrum is purified (FIG. 6(d)). The thus obtained mass spectrum is free of peaks other than the peak of the object component and can be easily verified compared with the one that has not been automatically purified. As a result, the reliability is improved. Referring back to FIG. 1, it is verified whether the apparatus is in a state in which it can be used for quantitative analysis (step 28, subroutine B). FIG. 7 is a flow-chart for verifying the state of the apparatus. First, referring to a data file for confirming the reliability that has been stored in advance, the current apparatus conditions, kinds of the samples to be measured, concentrations and the like are compared (step 122). When these measurement conditions are different, the different measurement conditions are displayed to prompt the operator to make the measurement again (step 126). When the measurement conditions are all equal, the procedure proceeds to the next verification. Next, the mass spectrum for confirming the reliability is compared with the mass spectrum of the reference sample (step 128). First, the peak intensity of the mass number for determination is compared. When the intensity differs greatly, an alarm is displayed indicating that the sensitivity is abnormal (step 130). When the intensity lies within a specific allowable range, the procedure proceeds to the next verification. Next, the degree of analogy is found between the two mass spectra, and it is verified whether the degree of analogy is greater than a predetermined value or not. A differential spectrum of the relative intensity is found between the mass spectrum for confirming the reliability and the mass spectrum of the reference sample (step 132). Next, the average value Ex of peak intensities of the differential spectrum and the standard deviation Sx are calculated (steps 134, 136), and the degree of analogy is calculated using a computing equation. Here, when the degree of analogy assumes a value of from 0 to 1 and when the spectra are perfectly the same, the constants A and B are so determined that the degree of analogy is 1 (step 138). When the degree of analogy found through such a procedure is smaller than a predetermined value (step 140), the apparatus is not suited for executing quantitative analysis due, for example, to contamination, and the alarm is displayed (step 144). When the degree of analogy is greater than a predetermined value, it is judged that the apparatus is in a state where it can be used for executing quantitative analysis (step 144).

Figure 8:
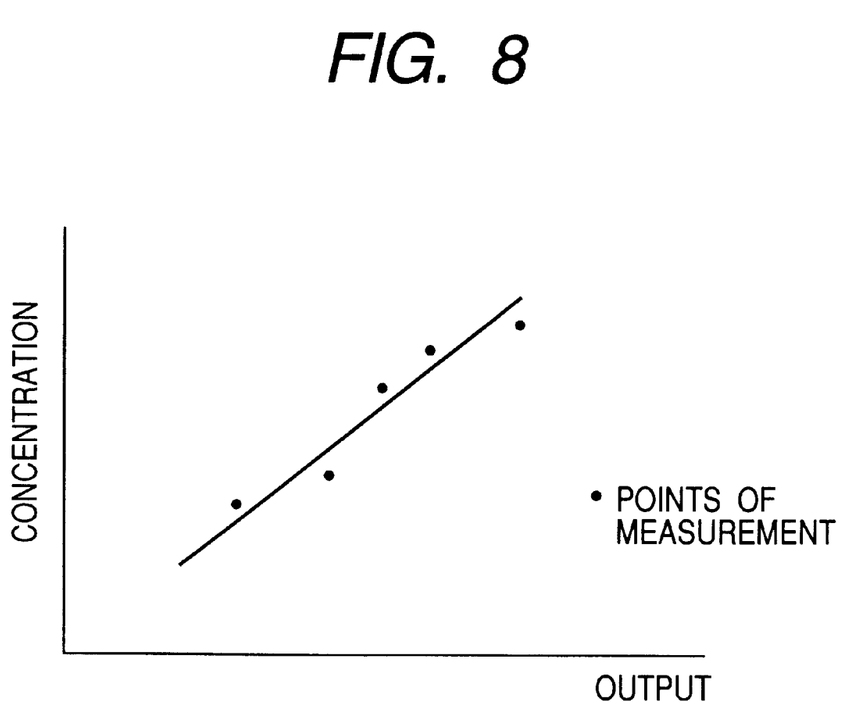
FIG. 8 is a diagram illustrating a calibration curve.

Referring back to FIG. 1, a calibration curve of the object component is prepared from the peak area value of the mass chromatogram of the mass number for determination of the reference sample (step 30). FIG. 8 shows a calibration curve. Next, a sample of which the concentration is unknown is measured (step 32), and the concentration of the object component in the sample is measured using the calibration curve that is prepared above (step 33).

Figure 9:
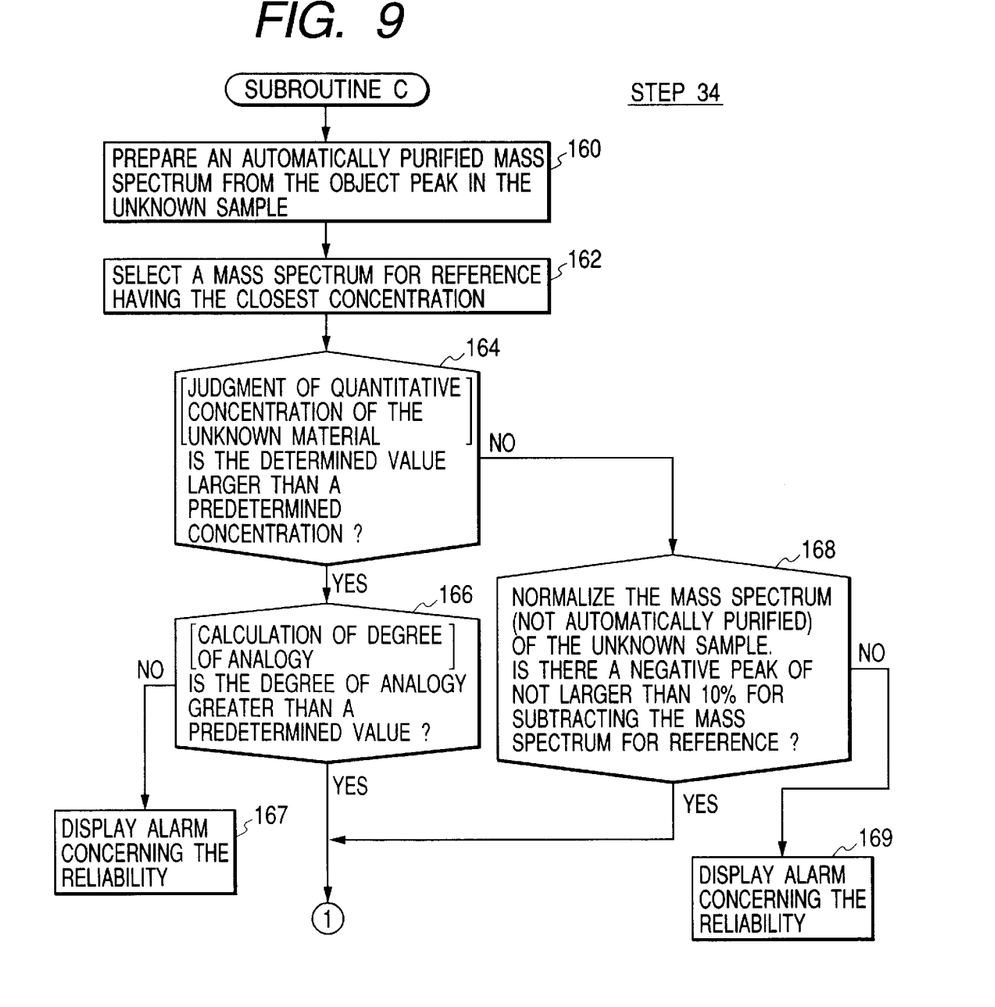
FIG. 9 is a flowchart (No. 1) illustrating, in detail, the verification of the reliability of the results of determination.
Figure 10:
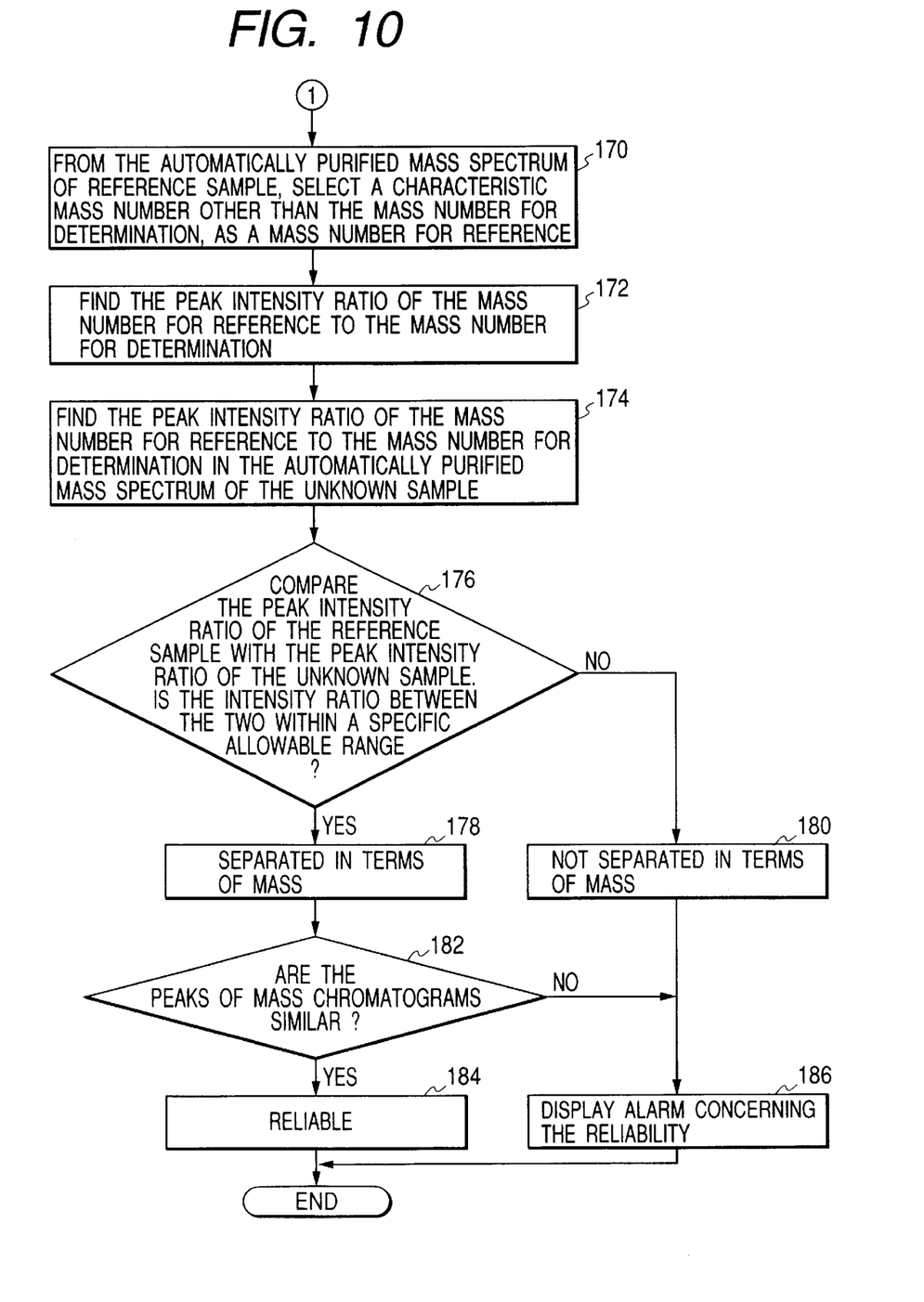
FIG. 10 is a flowchart (No. 2) illustrating, in detail, the verification of the reliability of the results of determination.
Figure 11:
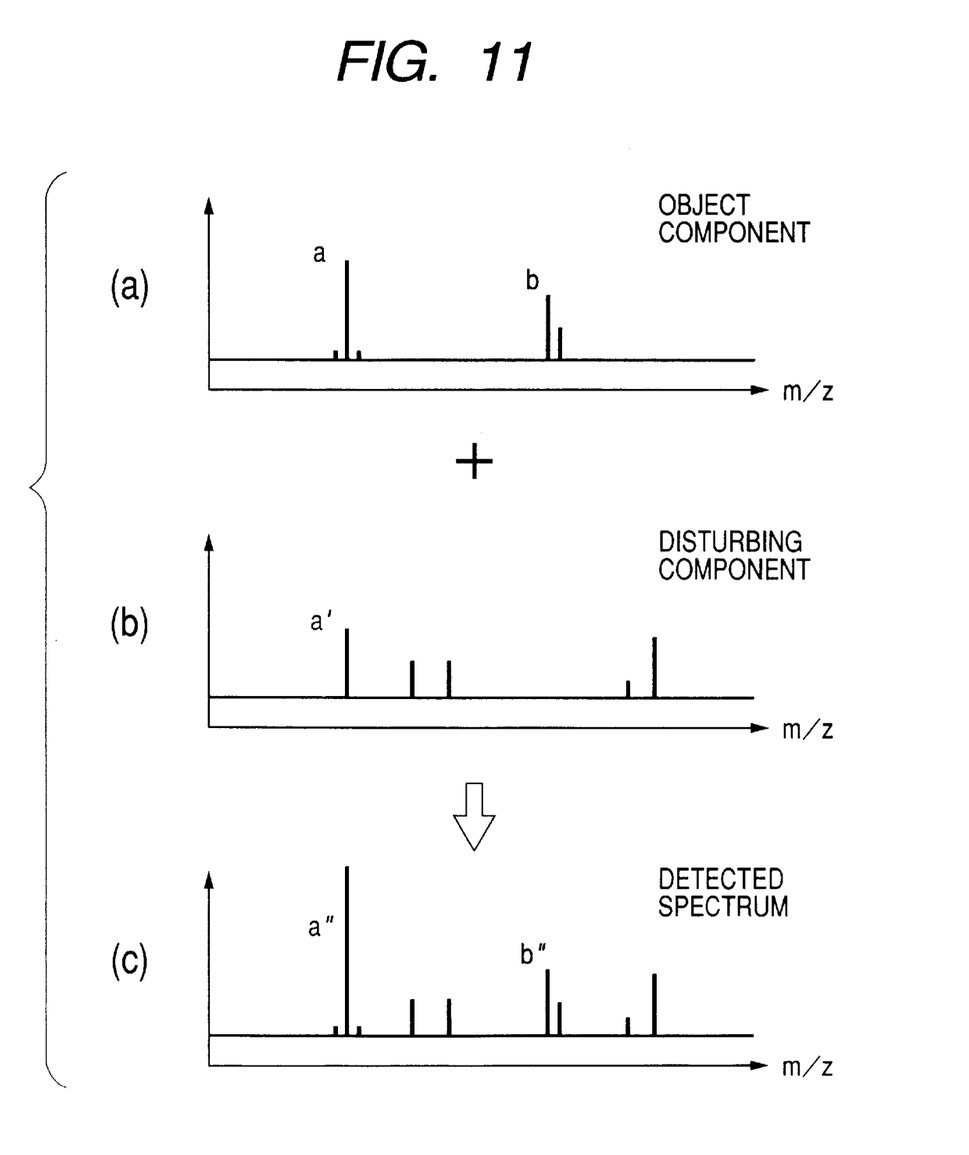

Here, the reliability of the results of determination is verified (step 34, subroutine C). FIGS. 9 and 11 are flow-chart for verifying the reliability. First, an automatically purified mass spectrum is prepared in the same manner as in the flowchart of FIG. 5 from the peak of the object component in the unknown sample (step 160). Here, the procedure is the same and is not described. Next, the mass spectrum of the reference sample having a concentration closest to that of the unknown sample is selected for reference (step 162). The concentration of the object component in the unknown sample is verified and, when the determined value is greater than a predetermined concentration, the reliability is verified using the degree of analogy. When the determined value is smaller than the predetermined concentration, the reliability is verified using the differential spectrum. This is because, the verification of reliability based upon the degree of analogy is very effective when the concentration of the object component is high. When the concentration of the object component is smaller than the predetermined concentration, however, the reliability of verification drops drastically. The verification of reliability based on the differential spectrum is slightly inferior to the one based on the degree of analogy, but can be adapted even when the concentration of the component is low. Therefore, when the concentration of the object component is greater than the predetermined value, the verification is effected relying upon the degree of analogy. When the concentration of the object component is smaller than the predetermined value, the verification is effected using the differential spectrum (step 164).

When the concentration of the object component is greater than the predetermined concentration, first, the degree of analogy of mass spectra of the reference sample and of the unknown sample is found in accordance with the flowchart of FIG. 7 (step 166). When the degree of analogy is smaller than a predetermined value, it is judged that the reliability is low (step 167). When the degree of analogy is larger than the predetermined value, the procedure proceeds to the step of verifying whether the mass number used for the determination has been separated or not. When the concentration of the unknown sample is smaller than a predetermined concentration, furthermore, the mass spectrum of the unknown sample of before being automatically purified is normalized, from which the mass spectrum for reference that is similarly normalized is subtracted. At this moment, it is verified whether there is a negative peak of not smaller than 10% (step 168). When there is a negative peak of not smaller than 10%, the possibility that the peak is not the one of the object component is high. It is therefore judged that the reliability is low, and an alarm is displayed (step 169). When there is no negative peak which is not smaller than 10%, it is then verified whether or not the mass number used for the determination has been separated like when the concentration is high.

Next, it is verified whether the mass number used for determination has been separated in terms of mass or not. First, from the mass spectrum of the reference sample that is automatically purified, the mass number of the peak attributed to the object component, other than the mass number for determination, is selected as a mass number for reference (step 170). Next, the peak intensity ratio of the mass number for reference to the mass number for determination is found (step 172). From the automatically purified mass spectrum of the unknown sample, similarly, the peak intensity ratio of the mass number for reference to the mass number for determination (step 174) is found, and their peak intensity ratios are compared. It is here verified whether their peak intensity ratios lie within a specific allowable range or not (step 176). When the peak intensity ratios lie outside the permissible range, it is judged that the mass number for determination is disturbed by something and has not been separated in terms of mass (step 180) and that the reliability of the results of determination is low, and an alarm is displayed (step 106). When the peak intensity ratios lie within the specific allowable range, the procedure proceeds to the step of verifying the degree of similarlity of the mass chromatograms. As shown, for example, in FIG. 11, when the peak ratio is greatly changed due to the application of a disturbing spectrum, it is judged that the reliability is low.

Next, verification of the degree of similarlity of peaks of the object component in the mass chromatograms of the reference sample and the unknown sample. The peak of the object component is selected from the mass chromatogram of the mass number for determination of the reference sample, and the half-width of the peak/the peak intensity is found. Similarly, the half-width of the peak/the peak intensity of the unknown sample is found, and it is verified whether they are equal to each other within the specific allowable range. When they are not equal, it is judged that the reliability is low. When they are equal within the specific allowable range, it is judged that the peak of the unknown sample is similar to the peak of the reference sample, and it is judged that the result of determination is reliable (steps 180, 184).

Figure 12:
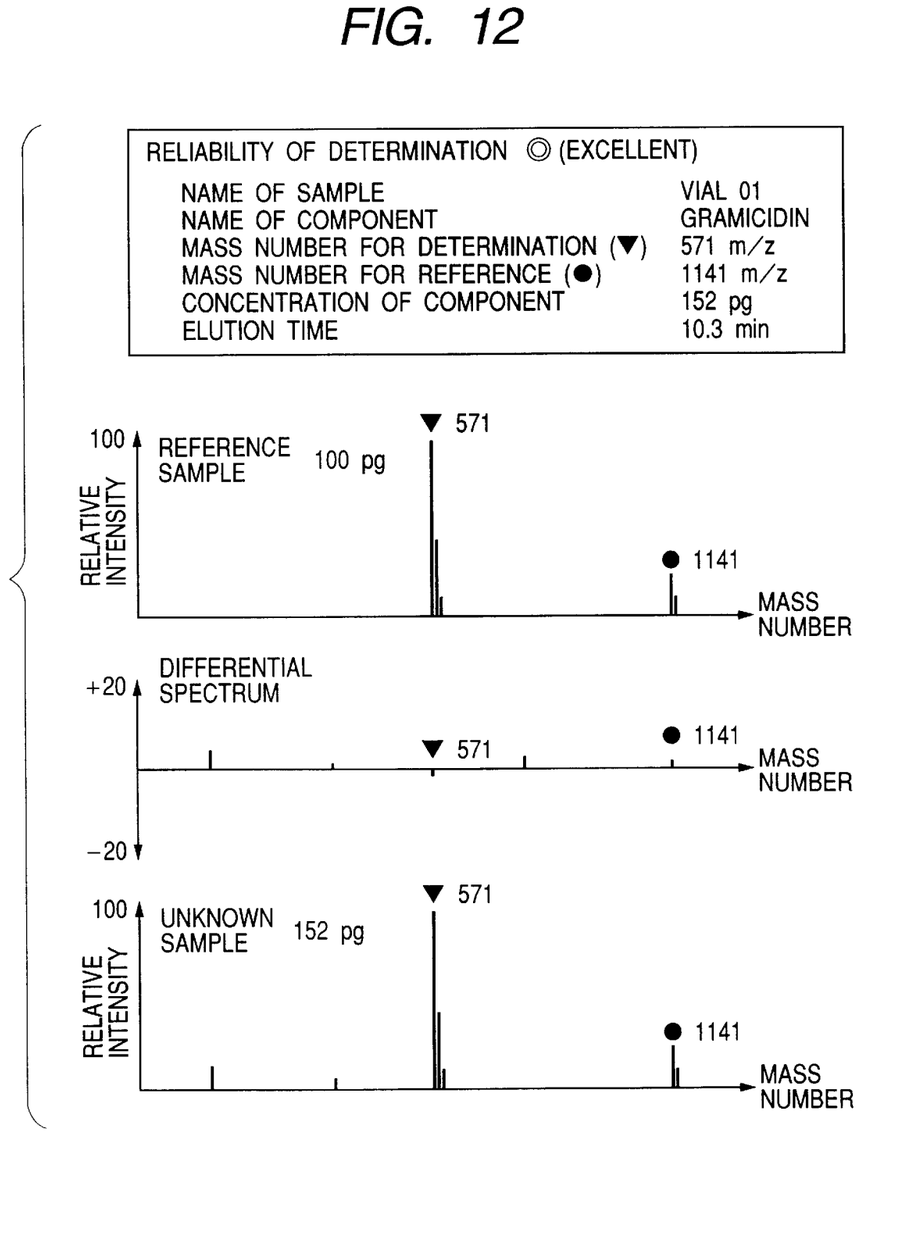
FIG. 12 is a diagram showing a display example that matches with the data processor.

Thereafter, the result of determination and the result obtained by verifying the reliability are output to the screen of the data processor 13. FIG. 12 shows an example of outputs of report of the results of verifying the reliability. The example of FIG. 12 is when the quantitative analysis is highly reliable; i.e., the double circle indicates that the determination is highly reliable. When it is judged that the reliability is low, a circle, a triangle or × is displayed depending upon the degree of reliability for easy grasp. Numerals may be displayed on the screen to indicate the degree of analogy used for verifying the reliability or the degree of mass separation. In this case, furthermore, the reason why the reliability is judged to be low may also be displayed by using numerals such as the degree of analogy or the degree of mass separation or by using words.

As shown in FIG. 12, furthermore, the normalized spectra of the mass spectrum of the reference sample and the mass spectrum of the unknown sample are displayed, or the differential spectrum between the two mass spectra is displayed at the time of outputting the results of report of reliability, making it possible to confirm the reliability using the results of determination or numerical values and using visual display, enabling the person who conducts the analysis to confirm the validity of the report of reliability. In this case, furthermore, the color may be changed, a mark may be attached or the kind of line may be changed for the mass number for determination and for the mass number for reference to make clear distinction from other mass numbers. Therefore, the person who conducts the analysis can visually and easily make sure whether the object component is separated in terms of mass or not. In FIG. 12, a black triangle is attached to a portion of the mass number for determination and a black circle is attached to a portion of the mass number for reference, to make clear distinction from other mass numbers.

In the determination by using the mass spectroscope as described above, whether the result of determination of the unknown sample is correctly the result of the object component or not is verified by the comparison of the mass spectrum of the reference sample with the mass spectrum of the unknown sample and is judged using numerical values.

Therefore, anybody can obtain the same judgment irrespective of the degree of skill of the person who conducts the analysis. Besides, comparison of the reference spectrum having a concentration closest to that of the unknown sample makes it possible to minimize the influence of change in the spectrum pattern caused by the concentration. By conducting verification by using the automatically purified spectrum from which the influence of the background, the random noise and the adjacent peaks are automatically removed, for calculating the degree of analogy, furthermore, it is possible to ensure a higher reliability. By verifying the degree of similarlity of the mass chromatogram, furthermore, it is possible to verify the change in the shape of peaks in the chromatogram caused by contamination of the column. By verifying the state of mass separation of the mass number for determination, furthermore, it is possible to judge the disturbance due to other components.

The above-mentioned results of judgment are displayed on the screen as a report of reliability. Therefore, the person who conducts the analysis can confirm the reliability of the results of determination by reading the numerical values and further can confirm it visually. Moreover, the report may be printed and attached to the results of determination to prove the reliability.

By verifying the state in which the apparatus is placed prior to measuring the unknown sample, the reliability of the results of determination is improved, and wasteful measurement is suppressed that may result from an abnormal state of the apparatus.

As described above, the present invention improves the reliability in mass spectrometry.

What is claimed is:

1. A mass spectrometry method comprising the steps of:
   separating an object component from a sample;
   obtaining a mass chromatogram of the object component;
   obtaining a mass spectrum of the object component;
   wherein the mass spectrometry method further comprises the step of:
   comparing the mass chromatogram of the object component with a mass chromatogram generated for each peak on the mass spectrum of the object component.

2. A mass spectrometry method comprising the steps of:
   separating an object component from a sample;
   obtaining a mass chromatogram of the object component;
   obtaining a mass spectrum of the object component;
   wherein the mass spectrometry method further comprises the steps of:
   generating a mass chromatogram for each peak on the mass spectrum of the object component;
   comparing the mass chromatogram of the object component with the mass chromatogram generated for each peak on the mass spectrum of the object component;
   eliminating peaks from the mass spectrum of the object component which, for the same elution time, do not have corresponding peaks in the mass chromatogram generated for each peak on the mass spectrum of the object component.

3. A mass spectrometry method comprising the steps of:
   separating an object component from a sample;
   obtaining a mass chromatogram of the object component;
   obtaining a mass spectrum of the object component;
   the mass spectrometry method further comprising the step of:
   comparing the mass spectrum of the object component in the sample with the mass spectrum of a reference sample if the concentration of the object component in the sample is equal to or greater than a predetermined value; or, if the concentration of the object component in the sample is less than a predetermined value, obtaining a differential spectrum by subtracting a normalized mass spectrum of a reference sample from a normalized mass spectrum of the object component.

4. A mass spectrometry method comprising the steps of:

separating an object component from a sample;

obtaining a mass chromatogram of the object component;

obtaining a mass spectrum of the object component;

determining the concentration of the object component in the sample by preparing a calibration curve obtained from mass spectra of samples of known concentration, and, utilizing the calibration curve to determine the concentration of the object component in the sample;

the mass spectrometry method further comprising the step of:

comparing the mass spectrum of the object component in the sample with the mass spectrum of a reference sample if the concentration of the object component is equal to or greater than a predetermined value; or, if the concentration of the object component is less than a predetermined value, obtaining a differential spectrum by subtracting a normalized mass spectrum of a reference sample from a normalized mass spectrum of the object component and verifying whether the differential spectrum contains any negative peak of not smaller than 10%.

5. A mass spectrometry method comprising the steps of:

separating an object component from a sample;

obtaining a mass chromatogram of the object component;

obtaining a mass spectrum of the object component;

determining the concentration of the object component in the sample;

the mass spectrometry method further comprising the steps of:

comparing the mass chromatogram of the object component with a mass chromatogram generated for each peak on the mass spectrum of the object component;

and, comparing the mass spectrum of the object component in the sample with the mass spectrum of a reference sample if the concentration of the object component in the sample is equal to or greater than a predetermined value; or, if the concentration of the object component in the sample is less than a predetermined value, obtaining a differential spectrum by subtracting a normalized mass spectrum of a reference sample from a normalized mass spectrum of the object component.

6. A mass spectrometry method according to claim 5, further comprising the step of:

finding from a mass spectrum of a reference sample, the peak intensity ratio of a peak corresponding to a mass number selected for reference and a peak corresponding to a mass number for determination; and, finding from a mass spectrum of the object sample, the peak intensity ratio of a peak corresponding to the mass number for reference and peak corresponding to the mass number for determination; and, verifying whether the peak intensity ratios for the reference sample and the object sample are within an allowable range.

7. A mass spectrometry method according to claim 5, further comprising the step of:

before analyzing, verifying whether a mass spectrometer would be proper for quantitative analysis.

8. A mass spectrometry method according to claims 5, further comprising the step of:

displaying results of both quantitative analysis verification of the quantitative analysis.

9. A mass spectrometry method according to claim 8, wherein said displaying results of the quantitative analysis verification includes displaying at least a degree of intensity ratio.

10. A mass spectrometry method comprising the step of:

separating samples to every component;

ionizing the component;

separating the ionized components depending upon the mass;

measuring the amount corresponding to a specific mass contained in the component by the separation;

the mass spectrometry further displaying both mass spectrum of a standard sample and mass spectrum of the selected component, and results of quantitative analysis and information relating to a reliability of said results of quantitative analysis.

11. A mass spectroscopy system comprising:

a separator for separating an object component from a sample; and, a mass spectrometer;

the mass spectroscopy system further comprising:

comparing means to compare a mass chromatogram of an object component with a mass chromatogram of each peak of a mass spectrum of the object component.

* * * * *